(12) United States Patent
Feng et al.

(10) Patent No.: US 9,029,090 B2
(45) Date of Patent: May 12, 2015

(54) METHOD FOR AUXILIARY IDENTIFICATION OF INBRED LINE OF WUZHISHAN MINIATURE PIG AND ITS SPECIAL PRIMER

(75) Inventors: Shutang Feng, Beijing (CN); Kui Li, Beijing (CN); Yulian Mu, Beijing (CN); Shulin Yang, Beijing (CN)

(73) Assignee: Institute of Animal Science Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 13/147,361

(22) PCT Filed: Mar. 1, 2010

(86) PCT No.: PCT/CN2010/000252
§ 371 (c)(1),
(2), (4) Date: Jun. 1, 2012

(87) PCT Pub. No.: WO2011/106904
PCT Pub. Date: Sep. 9, 2011

(65) Prior Publication Data
US 2012/0315636 A1 Dec. 13, 2012

(51) Int. Cl.
C12Q 1/68 (2006.01)
A01K 67/027 (2006.01)

(52) U.S. Cl.
CPC ......... *A01K 67/027* (2013.01); *A01K 2227/108* (2013.01); *C12Q 1/6888* (2013.01); *C12Q 2600/124* (2013.01); *C12Q 1/6876* (2013.01)

(58) Field of Classification Search
USPC .......................................... 435/6.12; 204/540
See application file for complete search history.

(56) References Cited

U.S. PATENT DOCUMENTS 7,459,271 B2 * 12/2008 Siemering .................... 435/6.11

FOREIGN PATENT DOCUMENTS

| CN | 101139389 | * | 8/2007 | ............ C07K 14/47 |
| CN | 101532055 | A | 9/2009 | |
| CN | 101608237 | * | 12/2009 | ............... C12Q 1/68 |
| CN | 101608237 | A | 12/2009 | |

OTHER PUBLICATIONS

Genbank Accession No. AK232171 (Nov. 2007).*

Zheng et al., 2009, Analysis of SNPs in promoter region of growth hormone (GH) gene in minpigs. Xu mu shou yi xue bao journal. vol. 40, p. 639-644.*
Zhang et al., 2009, Cloning and sequence analysis on cDNA of growth hormone releasing hormone receptor gene from Wuzhishan miniature pig. Agricultural Science and Technology Journal. vol. 10, pp. 87-90.*
Li et al., 2009, Genetic variation of inbred families of Wuzhishan miniature pig using microsatellite DNA loci. Xu mu shou yi xue bao. vol. 40. pp. 296-302.*
Mo D, Zhu Z, te Pas MF, Li X, Yang S, Wang H, Wang H, Li K. Characterization, expression profiles, intracellular distribution and association analysis of porcine PNAS-4 gene with production traits. BMC Genet. 2008;9:40.*
International Preliminary Report on Patentability Chapter I for PCT/CN2010/000252 filed on Sep. 4, 2012.*
English translation of CN 101608237 (2009).*
GenBank Accession No. DQ406743 (Jul. 2008).*
English translation of CN 101139389 (2007).*
Buck et al. (1999). Design Strategies and performance of Custom DNA Sequencing primers. Biotechniques, 27, p. 528-536).*
Laganowska M, Kaznowski A. Restriction fragment length polymorphism of 16S-23S rDNA intergenic spacer of *Aeromonas* spp. Syst Appl Microbiol. Sep. 2004;27(5):549-57.*
Wang Li-Juan, Li Qiu-Ling, Wang Chang-Fa, Wang Hong-Mei, Li Jian-Bin, Gao Yun-Dong, Hou Ming-Hai and Zhong Ji-Feng (2009. Abstract). CRS-PCR polymorphisms of the GHR gene and its relationship with milk production traits in Chinese Holstein cows. Chinese Journal of Agricultural Biotechnology, 6, pp. 215-219.*
Delin Mo, "Characterization, expression profiles, intracellular distribution and association analysis of porcine PNAS-4 gene with production traits", BMC Genetics, 2008, vol. 9, issue 40, pp. 1-10.
International Search Report and Written Opinion for International Application No. PCT/CN2010/000252, dated Dec. 9, 2010.

* cited by examiner

*Primary Examiner* — Angela M Bertagna
*Assistant Examiner* — Olayinka Oyeyemi
(74) *Attorney, Agent, or Firm* — Knobbe, Martens, Olson & Bear, LLP

(57) ABSTRACT

A method for auxiliary identification of WZSP inbred line and its special primers are disclosed. The method may comprise: testing whether a deoxyribose nucleotide at site 1273 from 5' end of genomic DNA comprising SEQ ID NO: 1 in a test pig is A or G, measuring whether the test pig genotype is GG, GA or AA wherein the test pig with GG genotype is a candidate for the WZSP inbred line and the test pigs with GA genotype and AA genotype are non-WZSP inbred line. The method can be applied to breed WZSP inbred line, which can be used to preliminarily screen all the pigs in test pig group, eliminate non-WZSP inbred line, find out a candidate WZSP inbred line and make a further confirmation in combination with other methods. The method and primers can also be used to judge whether a WZSP on market is counterfeiting or not.

5 Claims, 1 Drawing Sheet

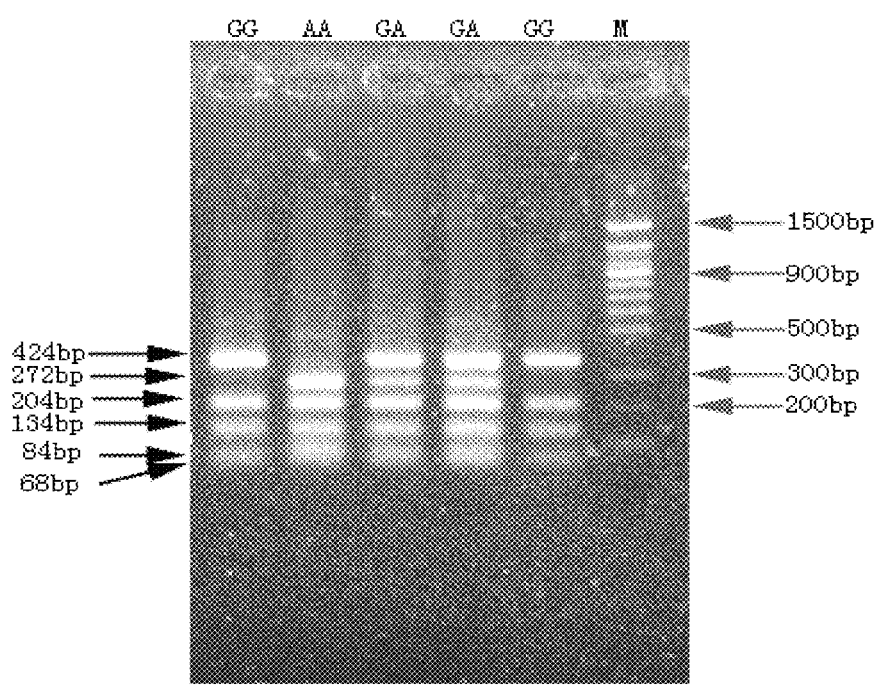

SEQUENCE LISTING

<160> NUMBER OF SEQ ID NOS: 3

<210> SEQ ID NO 1
<211> LENGTH: 3169
<212> TYPE: DNA
<213> ORGANISM: Sus scrofa

<400> SEQUENCE: 1

| | | | | | |
|---|---|---|---|---|---|
| tgaacgagta | cacctcatcc | atcggaattg | gagtttttca | ttcaggaatt | gaagtatatg | 60 |
| gcagaggtat | gtgtacacac | agtctaaatg | cattttctga | agattttcct | ccttaaaaa | 120 |
| gagttgtaaa | atcatgaaaa | cagctcttcc | tctttttttt | aatgcacttt | catgctttat | 180 |
| tgtagaaagt | agatgaaaat | ctccctgtat | ttgtttatat | ttgtatttca | gaaaaatgcc | 240 |
| ctaaattaaa | tgtatttggg | gagagagtac | tcagagtaca | tgggtatgca | ttgatttggt | 300 |
| tttctttat | tctaaatact | gtcttaaaaa | atattttcct | tttgagattg | ttataccatg | 360 |
| accatttcac | ttttatatat | attgaccttc | ctaagaaacc | ttgaacttca | aaaaatagtt | 420 |
| cccgttgtgg | ctcagcggaa | acgaatctga | ctagtatcca | cgaggacgtg | ggttcaatcc | 480 |
| ctggccttgc | tcagcgggtt | aaggatccac | attgccgtga | gttgtggtgt | aggtcgcaga | 540 |
| cgtggctccg | atgctgtggc | tgtggtgtag | gccggcagct | gcagttccaa | ttccacccct | 600 |
| agcttgggaa | cttccatata | tcacaggttc | ggccctaaaa | aagcaaaaaa | taaaaaataa | 660 |
| aaaaaaagta | aagagttccc | gtcatggctc | agtggttaac | gaatccgact | aggaaccatg | 720 |
| aggttgcagg | ttcaatccct | ggccttgctc | agtgggttaa | ggatccagcg | atgccatgag | 780 |
| ctgttgtgta | ggttgcagac | acggctcaga | tcccgagttg | ctgtgtctct | ggcataggcc | 840 |
| tgtggctaca | gctccaattc | gaccccctagc | ctgggacctc | cgtatgctgc | aggagcagcc | 900 |
| caagaaatgg | caaaaaaaaa | aagagagaga | gaaatagtat | gataaaaaca | atggttttgg | 960 |
| ttggaaaagg | attaatgcta | gagtgtcaaa | cttgtaatac | caatttcctg | agggaatttc | 1020 |
| agtaataaat | ttgtttttgt | agacctataa | gtgcataggg | atagttttaa | aatatctctg | 1080 |
| agcaaatcct | gcctttgatg | acatctagct | ttttgctcag | gattgatggc | ccttgtcatt | 1140 |
| aactcagccc | ttttattct | ttattacctt | tcactatgat | aagcataact | agaaccactc | 1200 |
| aaaccaagca | gctgtgtttc | cacaactttt | cctttgttct | cattctctct | cagtacaaga | 1260 |
| taatctgatc | aagttgtagg | tagtaatagt | ctgtgtaaaa | cagatgacat | ggctcgtttc | 1320 |
| atcaaggttg | tagtaatata | ctcgtttgca | tataaactac | cgtatagcac | caatgcttct | 1380 |
| gtctgcttca | gctgggcagt | cttggtggcc | tctcagccta | tggcattgca | ccttactccc | 1440 |
| agttacccct | gaggactaca | taccagcttt | ggctgataca | aagaaaaggc | tcatttactt | 1500 |
| gaatatgtta | gtgtggtgtt | tttctatccc | tttttttata | ggctgaatta | gctgcttctg | 1560 |
| ggtgcagtgc | tgtaaagatc | taccatgtta | agttctgttg | tacttggaag | actgcatcta | 1620 |
| ccaaataatc | ccccaaagca | gtgaagttcc | cgcagaaagt | ttcagtggtt | agagtattga | 1680 |
| tatgggtggc | tttgctccct | gtttgacttg | gcttttgcca | cagttggcgt | atacattcct | 1740 |
| ttttacccga | atttgtatgt | tgtgttacag | tttttaaaag | taccaccaag | ttttgtacga | 1800 |
| catgaccatg | ccggtctgag | gtagatggga | gcatttttca | gatgaaactg | aagctcagac | 1860 |
| ctgctaaaag | tgctactgcg | aataattaac | agaactagga | cctgacccct | agtgtcatat | 1920 |
| actaacccgt | tatcctttta | cctgcctgat | cattgttccc | attcagaaaa | tgacttagga | 1980 |
| ataattagaa | atatgtttca | gaacagcaag | gccagggcca | gatacattcc | taaaagtgaa | 2040 |
| ttgtttctag | aatagaaggg | caagtgggcc | tacactttcc | ttgctataat | tgagacatta | 2100 |

-continued

```
aaaaatctaa atatgatctt gccatggcta tctaacctta tctacaatgt tttataaaat    2160
tctccattaa aaattttaa tgtatatttc agaatttaat gctgaacact ttcttattct     2220
acattttgct tcttttctg aaagatctga atcagaagta aggttagaat tgccttattc     2280
tttcccatgt tttgttctaa gaccttaaaa gattacattt aataaattct aagtgatgag    2340
attaatttaa gcaattgttt ggaattcttt aaatctacta agatttgcca cctaaatatc    2400
taagtatctc atgtcagaat tgtagccaga aattttagtt ccttcctgat ttgaaaccat    2460
tctccatttt tgtgctggat gagagtttat atctgatgag cctggaaata cattcactat    2520
agttctcttc tagcttaaag atgtgctgtg gagtgtgtgt gtgtgtgtta attttgcagc    2580
ttatcttttc ttgaatgaga ggaattgaat tcagtttttc aggtttgcta atgtttcact    2640
cttacccaaa gataagccaa gaatcttcat cccaggaacc atgaaaactc atggttatta    2700
aacagttttt ccagtaaagt tcaagtttga aatttggtca tttgaagtta gaaagtggca    2760
aaccactgaa gcacccacct acttacttga gcatgatcga taaacacgcg gatctttgag    2820
tgttagtcac tctcctccag ccagaataaa taaatataca aatcaggatc acctttgagt    2880
gtcttttgtt attagagttt caagtctctt acatcaacta ttctattcaa gtagtagaat    2940
aaaatactaa atgaaatatt tgtgaaagca ttaaactgaa aaatatttag atggtatcat    3000
tattatcctc atcatttatt aaagctaatt cagcatactg gttaaatttt atgtgataaa    3060
tactaaaaat catgagtttt ctcttttcag agtttgctta tggtggccat ccttacccct    3120
tttctggaat atttgaaatt tccccaggaa atgcttctga actaggaga               3169
```

<210> SEQ ID NO 2
<211> LENGTH: 24
<212> TYPE: DNA
<213> ORGANISM: Artificial sequence
<220> FEATURE:
<223> OTHER INFORMATION: nucleotide sequence of primer

<400> SEQUENCE: 2
ctagaaccac tcaaaccaag cagc                                            24

<210> SEQ ID NO 3
<211> LENGTH: 24
<212> TYPE: DNA
<213> ORGANISM: Artificial sequence
<220> FEATURE:
<223> OTHER INFORMATION: nucleotide sequence of primer

<400> SEQUENCE: 3
atcaggcagg taaaaggata acgg                                            24

METHOD FOR AUXILIARY IDENTIFICATION OF INBRED LINE OF WUZHISHAN MINIATURE PIG AND ITS SPECIAL PRIMER

RELATED APPLICATIONS

This application is a U.S. National Phase of International Application No.: PCT/CN2010/000252, filed Mar. 1, 2010, designating the U.S. The International Application was filed in Chinese and has not been published as of the filing date of the present U.S. National Phase application.

TECHNICAL FIELD

This invention relates to a method for auxiliary identification of WUZHISHAN miniature pig (WZSP) inbred line and its special primers.

TECHNICAL BACKGROUND

In early period of China's reform and opening up, the researcher, when studying in West Germany in 1983-1984, had a great privilege to visit the West Germany Gottengen Miniature Pig Breeding Center. The researcher learned that the miniature pig, which had been marketed in many countries and regions, was widely applied to Animal Models of Human Diseases in many western countries, and was also a great subject for the study of porcine embryonic. The Research then had the idea of introducing Gottengen Miniature Pig into China for development and application. Professor Smith, an expert in Gottengen Miniature Pig Breeding, was interested in Chinese MEISHAN pig. He suggested that the West German Ministry of Agriculture put the Gottengen Miniature Pig as a special support for bilateral cooperation, and the researchers also got support from Ministry of Agriculture after returning to China. But the plan was not carried out for various reasons, the key of which is that West Germany was reluctant to provide China the pig resources through research cooperation. In the meantime, the researcher found a large number of specific animal species such as WUZHISHAN PIG (WZSP) in China after a large-scale animal species resource investigation. WZSP are endangered species (see the Investigation Report by Feng Weiqi researcher from China Academy of Agricultural Sciences, Wang Zheng from Institute of Animal Husbandry of Guangdong Province et al, July 1987). From the data, it is showed that the miniaturization characteristics, genetic stability of WZSP are much better than that of West Germany Gottengen Miniature Pig, indicating it has promising prospects for application.

Since 1987, with the support from the Ministry of Agriculture, National Science and Technology Department of China, National Natural Science Foundation of China, et al., Institute of Animal Husbandry of Chinese Academy of Agricultural Sciences made efforts for 20 years and invested 15 million yuan to obtain the miniature pig of WZSP for the first time in the world by using, isolating and breeding the WZSP with small size, which has been passed to the 20$^{th}$ generation ($F_{20}$). WUZHISHAN Miniature pigs were subjected to inbred breeding for more than 10 generations from full-sib families, offspring-parent or three generations of WZSP, WZSP inbred group was obtained. The experiment proved that WZSP inbred group is highly homozygous in genes and genetically very stable and was named WZSP inbred-line (ZL02149030.9). The resulted WZSP inbred pigs have a docile temperament, clear genetic background, highly homozygous gene, black and white in color, size and coat color consistency compared to the original breeding herd. The WZSP inbred pigs also have advantages of smaller size, the genetic stability et al. compared to domestic and foreign varieties, which belong to new animal genetic resources, and have been listed as a national conservation farms (C1101001). A deep-level, multi-faceted study and exploitation as well as utilization in human Comparison medicine, such as Transplantation for Burned Skin, Cardiovascular Model, Oral Tooth Diseases, xenograft of organs and so on, are made. The result indicates: the WZSP inbred pig is not only a good source for pig breeding and high-grade meat processing, but also is the best choice for experimental animal models. WZSP inbred line will play a special role and will make a great contribution to human medical research, xenotransplantation research.

INVENTION DISCLOSURE

The purpose of this invention is to provide a method for auxiliary identification of WZSP inbred line and its special primers.

The present invention provides a method for auxiliary identification of WZSP inbred line and/or Non-WZSP line. The method is used to test whether a deoxyribose nucleotide at site 1273 from 5' end of genomic DNA comprising SEQ ID NO: 1 (GenBank Accession Number DQ406743) in a test pig is A or G, to determine whether the genotype of the test pig is GG, GA or AA; wherein the GG genotype is a homozygote in which the deoxyribose nucleotide at site 1273 of SEQ ID NO: 1 is G; the AA genotype is homozygote in which the deoxyribose nucleotide at site 1273 of SEQ ID NO: 1 is A; and the GA genotype is their heterozygote;

the test pig with GG genotype is a candidate for the WZSP inbred line;

the test pigs with GA genotype and AA genotype are non-WZSP inbred line.

The method used to determine whether the deoxyribose nucleotide at site 1273 from 5' end of SEQ ID NO: 1 (GenBank Accession Number DQ406743) of genomic DNA in the test pig is G or A comprises the following steps: extracting genomic DNA, performing a polymerase chain reaction (PCR) with the extracted genomic DNA and a pair of primer; cutting DNA with a restriction enzyme; and electrophoresis.

The primer pair for PCR amplification is configured such that a product produced by PCR amplifying the pig genomic DNA as a template contains a deoxyribose nucleotide at site 1273 from 5' end of SEQ ID NO: 1 (GenBank Accession Number DQ406743) of the test pig.

Specifically, the primer pair for PCR amplification is a primer pair consisting of an oligonucleotide set forth in SEQ ID NO: 2 and an oligonucleotide set forth in SEQ ID NO: 3.

The restriction enzyme used in the enzyme cut is TasI. The electrophoresis is specifically conducted in an agarose gel. For the pig with GG genotype, PCR-RFLP testing (TasI enzyme cut) shows four bands after electrophoresis: 357 bp, 204 bp, 134 bp and 67 bp in sequence length, respectively; for the pig with AA genotype, PCR-RFLP (TasI enzyme cut) shows five bands after electrophoresis: 82 bp, 275 bp, 204 bp, 134 bp and 67 bp in sequence length, respectively; for the pig with GA genotype, PCR-RFLP (TasI enzyme cut) shows six bands after electrophoresis: 357 bp, 82 bp, 275 bp 204 bp, 134 bp and 67 bp in sequence length, respectively.

This invention also seeks to protect a primer pair for assistant identification of WZSP inbred line and/or non WZSP inbred line, the primer pair is configured such that a product by PCR amplifying the pig genomic DNA as a template contains a deoxyribose nucleotide at site 1273 from 5' end of SEQ ID NO: 1.

Specifically, the primer pair is a primer pair consisting of an oligonucleotide set forth in SEQ ID NO: 2 and an oligonucleotide set forth in SEQ ID NO: 3.

The primer pair can be used in the preparation of kit for assistant identification of WZSP inbred line and/or non WZSP inbred line.

The primer pair can be used in the preparation of an agent for assistant identification of WZSP inbred line and/or non WZSP inbred line.

This invention also seeks to protect a kit for auxiliary identification of WZSP inbred line and/or non WZSP inbred line, the kit comprises the primer pair mentioned above. The kit further includes reagents for PCR and reagents for electrophoresis.

The kit or the primer pair of the present invention can be applied to assist identification of WZSP inbred line and/or non WZSP inbred line.

The kit, the primer and the method of the present invention can be applied in pig breeding.

In the kit, the primer, the method and the uses of the present invention, the WZSP inbred line can be $F_{13}$ to $F_{20}$ generation.

DESCRIPTION OF FIGURES

FIG. 1 is Restriction endonuclease map of three genotypes samples; M: DNA molecular weight standard (100-1500 bp ladder).

FIG. 1

The Best Mode for Carrying Out the Invention

The following examples are used for better understanding of the invention, but not to limit the invention. The experimental methods of the following examples are conventional methods, unless noted otherwise. Without special instructions, the test materials used in the following examples, all were purchased from conventional biochemical reagents shop.

WZSP inbred line (Li Kai; Mou Yulian; Han Jianlin; Yang Shulin; Liu Lan; Yuan Xinxu; Guo Yong; Feng Shutang, Study on Genetic Variation of Inbred Families of WZSP Using Microsatellite DNA Loci, Chinese Journal of Animal and Veterinary Sciences, 3$^{rd}$ 2009).

Example 1

Discovery of G1273A Polymorphisms of Pnas-4 Gene

The pigs used in experiment: 42 Guizhou Miniature Pigs, 49 Guangxi Bama Miniature Pigs and 42 WZSP inbred line.
1. PCR Amplification According to the second intron sequence of Pnas-4 genes (GenBank Accession Number DQ406743) (SEQ ID NO: 1 in sequence listing), a primer pair is designed as follows:

Upstream primer (the SEQ ID NO: 2 in sequence listing): 5'-CTAGAACCACTCAAACCAAGCAGC-3';

Downstream primer (the SEQ ID NO: 3 in sequence listing): 5'-ATCAGGCAGGTAAAAGGATAACGG-3'.

Using the above primer pair, a PCR amplification is conducted with the pig genomic DNA as a template.

Polymerase chain reaction (PCR) system: 2.0 µL 10× reaction buffer, 1.6 µL MgCl$_2$ (2.5 mmol/L), 1 µL upstream primer (10 µmol/L), 1 µL downstream primer (10 µmol/L), 0.4 µL dNTPs (10 mmol/L), 0.2 µL Taq enzymes, 1 µL templates, ddH$_2$O is added to a final volume of 20 µL.

PCR amplification procedure: 95° C. 3 min, 94° C. 20 s, 62.5° C. 30 s, 72° C. 30 s for 30 cycles, and finally extensions at 72° C. for 3 min.

Amplification product is identified by electrophoresis on 1.5% AGAR gel.
2. RFLP Analysis Endonuclease Reaction system (10 µL): 1× buffer 1 µL, PCR products 5 µL, restriction enzymes TasI 0.5 µL (5 U), and H$_2$O is added to a volume of 10 µL.

After the enzyme cut is conducted for eight hours, 1.5% agarose gel electrophoresis is used to detect the results of enzyme cut.

The products produced after enzyme cut presented three band types. Part of samples show four bands after electrophoresis with a the sequence length of 357 bp, 204 bp, 134 bp and 67 bp, respectively; part of samples show five bands after electrophoresis with a sequence length of 82 bp, 275 bp, 204 bp, 134 bp and 67 bp, respectively; the remaining samples show six band after electrophoresis with a sequence length of 357 bp, 82 bp, 275 bp, 204 bp, 134 bp and 67 bp, respectively.
3. The Clone Sequencing and Sequence Analysis According to the PCR-RFLP analysis result, the PCR amplicon of sample displaying different bands after electrophoresis is respectively recovered and purified with agarose gel recovery kit (Tiangen biochemical technology Co., LTD.). After the recovered DNA fragment is ligated to a vector pGEM-T (Promega company), in accordance with Cohen's et al. method (*Proc Natl Acad Sci*, 69:2110), the ligation product is transformed into *E. coli* DH5α competent cells. According to carboxybenzylepenicillin resistance markers, positive clone is screened; the recombinant plasmids containing the recovered fragment are obtained. The recombinant plasmid is sequenced using the T7 and SP6 promoter sequences on this recombination as primer, The sequencing results show that the lengths of fragments from different samples are all 762 bp, in which only one difference of deoxyribose nucleotide (G/A) exists. This deoxyribose nucleotide is the one at site 1273 from 5' end of GenBank Accession Number DQ406743, named G1273A. The nucleotide sequence of the amplification fragment that deoxyribose nucleotide at site 1273 is G is set forth in SEQ ID NO: 1 in sequence listing.

According to the sequencing result and PCR-RFLP result, the genotype is defined as follows:

If the alleles at this site is G, the genotype of its homozygote is GG, and the PCR-RFLP testing (TasI enzyme cut) shows four bands after electrophoresis with the sequence's length of 357 bp, 204 bp 134 bp and 67 bp, respectively;

If the alleles at this site is A, the genotype of its homozygote genotype is AA, and the PCR-RFLP testing (TasI enzyme cut) shows five bands after electrophoresis with the sequence's length of 82 bp, 275 bp, 204 bp 134 bp and 67 bp, respectively;

The genotype of the heterozygote for this site is GA, and the PCR-RFLP (TasI enzyme cut) testing shows six bands after electrophoresis with the sequence's length of 357 bp, 82 bp, 275 bp 204 bp, 134 bp and 67 bp, respectively.

The primer pair of the invention is used to amplify the genomic DNA of test pig, a 762 bp fragment is obtained. If the deoxyribose nucleotide at site 1273 from 5' end of GenBank Accession Number DQ406743 is A, the fragment of 357 bp is cleaved into fragments of 82 bp and 275 bp after cutting with restriction enzymes TasI.

The restriction endonuclease map of three genotypes samples is shown in FIG. 1.

The detection results of genotypes from different varieties of pigs are shown in Table 1.

TABLE 1

TasI polymorphism test results of Pnas-4 gene of different varieties of pig

| Variety | Number | Genotype | | | Genotype Frequency | | | Allele Frequencies | |
|---|---|---|---|---|---|---|---|---|---|
| | | GG | GA | AA | GG | GA | AA | G | A |
| Guizhou Mini Pig | 42 | 31 | 11 | 0 | 0.738 | 0.262 | 0.000 | 0.87 | 0.13 |
| Guangxi Bama Mini Pig | 49 | 2 | 14 | 33 | 0.041 | 0.286 | 0.673 | 0.18 | 0.82 |
| WZSP | 42 | 42 | 0 | 0 | 1.000 | 0.000 | 0.000 | 1.000 | 0.00 |

Results show that the WZSP inbred line only has GG genotype and G alleles, while other varieties of miniature pigs has A allele.

The inventors found a polymorphism site, at which WZSP has only G allele while other varieties of pigs have A alleles. So this polymorphism site can be used to screen test pigs. If the test pig has a GG genotype, it can be used as a candidate WZSP line; if the test pig has a GA genotype or a AA genotype, it is certainly not a WZSP inbred line. The method of the present invention can be used to breed WZSP inbred line. All the pigs in test pig population can be subjected to preliminary screening in advance, the non-WZSP is eliminated, and the candidate WZSP inbred line is obtained which can be further confirmed with other methods. The present invention can also be used to detect whether the WZSP on market is counterfeiting or not.

Example 2

Use of G1273A Polymorphisms of Gene Pnas-4

Pig ear skin tissue samples are all collected from WZSP inbred line from Beijing Institute of Animal Husbandry and Veterinary, the Chinese Academy of Agricultural Sciences, in which $F_{13}$ (generation) 15 (pigs), $F_{14}$ 13 (pigs), $F_{15}$ 11 (pigs), $F_{16}$ 14 (pigs), $F_{17}$ 14 (pigs), $F_{18}$ 14 (pigs), $F_{19}$ 15 (pigs), $F_{20}$ 15 (pigs), all the samples are freezed in −20° C. for DNA extraction after being treated with 75% ethanol.

1. PCR Amplification

The primers for PCR are as follows:

```
Upstream primer
(SEQ IN NO: 2 of the sequence listing):
5'-CTAGAACCACTCAAACCAAGCAGC-3';

Downstream primer
(SEQ IN NO: 3 of the sequence listing):
5'-ATCAGGCAGGTAAAAGGATAACGG-3'.
```

PCR amplification is conducted with pig genomic DNA as a template using the above primer pair.

Polymerase chain reaction (PCR) system: 2.0 μL 10× reaction buffer, 1.6 μL MgCl$_2$ (2.5 mmol/L), 1 μL upstream primer (10 μmol/L), 1 μL downstream primer (10 μmol/L), 0.4 μL dNTPs (10 mmol/L), 0.2 μL Taq polymerase 1 μL templates, ddH$_2$O is added to a final volume of 20 μL.

PCR amplification procedure: 95° C. 3 min, 94° C. 20 s, 62.5° C. 30 s, 72° C. 30 s, for 30 cycles, finally extensions at 72° C. for 3 min.

Amplification product is identified by electrophoresis on 1.5% AGAR gel.

2, RFLP Analysis

Endonuclease Reaction system (10 μL) is as follows: 1× buffer 1 μL, PCR products 5 μL, restriction enzymes TasI 0.5 μL (5 U), H$_2$O is added to a final volume of 10 μL.

After the enzyme cut is conducted for 8 hours, the enzyme cut result is detected by electrophoresis with 1.5% agarose gel, and the best quality images are obtained through the gel imaging system, the genotypes are recorded.

Results are shown in table 2.

TABLE 2 genotype test results of different generations of WZSP inbred line

| Generation | Number | Genotype | | | Genotype Frequency | | | Allele Frequencies | |
|---|---|---|---|---|---|---|---|---|---|
| | | GG | GA | AA | GG | GA | AA | G | A |
| $F_{13}$ | 15 | 15 | 0 | 0 | 1.000 | 0.000 | 0.000 | 1.000 | 0.000 |
| $F_{14}$ | 13 | 13 | 0 | 0 | 1.000 | 0.000 | 0.000 | 1.000 | 0.000 |
| $F_{15}$ | 11 | 11 | 0 | 0 | 1.000 | 0.000 | 0.000 | 1.000 | 0.000 |
| $F_{16}$ | 14 | 14 | 0 | 0 | 1.000 | 0.000 | 0.000 | 1.000 | 0.000 |
| $F_{17}$ | 14 | 14 | 0 | 0 | 1.000 | 0.000 | 0.000 | 1.000 | 0.000 |
| $F_{18}$ | 14 | 14 | 0 | 0 | 1.000 | 0.000 | 0.000 | 1.000 | 0.000 |
| $F_{19}$ | 15 | 15 | 0 | 0 | 1.000 | 0.000 | 0.000 | 1.000 | 0.000 |
| $F_{20}$ | 15 | 15 | 0 | 0 | 1.000 | 0.000 | 0.000 | 1.000 | 0.000 |

The results show that there is only GG genotype in $F_{13}$ to $F_{20}$ generations.

INDUSTRIAL APPLICATION

The inventor discovers that WZSP inbred line is homozygous at G1273A polymorphic site, and only GG genotype exits in the WZSP inbred line whereas other varieties of miniature pigs have GA and AA genotypes. So this polymorphism site can be used to screen test pigs. If a test pig has a GG genotype, it can be used as candidate WZSP line, if a test pig has a GA genotype or a AA genotype, it is certainly not a WZSP inbred line. The method of the present invention can be applied to breed WZSP inbred line. All the pigs in test pig population can be subjected to preliminary screening in advance, and the non-WZSP is eliminated, thus the candidate WZSP inbred line is found out, which can be further confirmed with other methods. The present invention can also be used to detect whether the WZSP on market is counterfeiting or not.

What is claimed is:

1. A method of breeding a Wu Zhishan miniature pig (WZSP) inbred line, comprising:
   providing a plurality of test lines of potential WZSP;
   providing a sample comprising genomic DNA of each of the plurality of test lines of potential WZSP;
   performing a polymerase chain reaction (PCR) with the genomic DNA and a pair of primers so as to obtain amplified DNA sequences, wherein said amplified DNA sequences contain the deoxyribose nucleotide corresponding to a deoxyribose nucleotide at site 1273 from the 5' end of SEQ ID NO: 1 in the genomic DNA of each of the plurality of test lines of potential WZSP;
   cutting the amplified DNA sequences with TasI;
   electrophoresing the amplified DNA that was cut with TasI;
   determining a genotype of each of the plurality of test lines of potential WZSP as GG, GA or AA based on a restriction fragment length polymorphism (RFLP) profile detected from said electrophoresis, wherein said GG genotype is a homozygote in which the deoxyribose nucleotide corresponding to a deoxyribose nucleotide at site 1273 from the 5' end of SEQ ID NO: 1 in the genomic DNA is G, said AA genotype is homozygote in which the deoxyribose nucleotide corresponding to a deoxyribose nucleotide at site 1273 from the 5' end of SEQ ID NO: 1 in the genomic DNA is A, and said GA genotype is their heterozygote;

removing test line(s) of potential WZSP having the GA genotype or AA genotype; and breeding test lines of potential WZSP having the GG genotype so as to produce a WZSP inbred line.

2. The method according to claim 1, wherein the primer pair for the PCR is a primer pair consisting of the oligonucleotide set forth as SEQ ID NO: 2 and the oligonucleotide set forth as SEQ ID NO: 3.

3. The method according to claim 2, wherein determining the genotype of each of the plurality of test lines of potential WZSP pig comprises: matching the RFLP profile to one of the following:

(a) a profile comprising electrophoresis bands of 357 bp, 204 bp, 134 bp, and 67 bp, but excluding 275 bp in sequence length;

(b) a profile comprising electrophoresis bands of 82 bp, 275 bp, 204 bp, 134 bp, and 67 bp in sequence length; and (c) a profile comprising electrophoresis bands of 357 bp, 82 bp, 275 bp, 204 bp, 134 bp, and 67 bp in sequence length; and determining the genotype of the test pig as follows:

determining the genotype of the test pig is GG if the RFLP profile corresponds to said profile (a);

determining the genotype of the test pig is AA if the RFLP profile corresponds to said profile (b);

and determining that the genotype of the test pig is GA if the RFLP profile corresponds to said profile (c).

4. The method according to claim 1, wherein said electrophoresing the amplified DNA is conducted on an agarose gel.

5. The method according to claim 1, wherein the WZSP inbred line is $F_{13}$ to $F_{20}$ generation.

* * * * *